(12) United States Patent
Rantala

(10) Patent No.: US 7,646,081 B2
(45) Date of Patent: Jan. 12, 2010

(54) LOW-K DIELECTRIC MATERIAL

(75) Inventor: Juha T. Rantala, Espoo (FI)

(73) Assignee: Silecs Oy, Espoo (FI)

( * ) Notice: Subject to any disclaimer, the term of this patent is extended or adjusted under 35 U.S.C. 154(b) by 431 days.

(21) Appl. No.: 10/563,801

(22) PCT Filed: Jul. 8, 2004

(86) PCT No.: PCT/FI2004/000440

§ 371 (c)(1), (2), (4) Date: Sep. 20, 2006

(87) PCT Pub. No.: WO2005/004221

PCT Pub. Date: Jan. 13, 2005

(65) Prior Publication Data

US 2007/0190800 A1 Aug. 16, 2007

Related U.S. Application Data

(60) Provisional application No. 60/485,114, filed on Jul. 8, 2003, provisional application No. 60/531,672, filed on Dec. 23, 2003.

(51) Int. Cl.
*H01L 23/58* (2006.01)
(52) U.S. Cl. .................. 257/642; 257/E23.12; 438/780
(58) Field of Classification Search .................. 438/780; 257/642, 780, E23.12
See application file for complete search history.

(56) References Cited

U.S. PATENT DOCUMENTS

| 2002/0004298 A1 | 1/2002 | Sugahara et al. | 438/623 |
| 2002/0076944 A1 | 6/2002 | Wang et al. | 438/780 |
| 2004/0038514 A1* | 2/2004 | Hyodo et al. | 438/623 |
| 2005/0130404 A1* | 6/2005 | Moghadam et al. | 438/623 |

FOREIGN PATENT DOCUMENTS

| EP | 0 713 927 A1 | 5/1996 |
| WO | 2004/027110 A2 | 4/2004 |

OTHER PUBLICATIONS

Saito, N. et al., "Surface potential images of self-assembled monolayers patterned by organosiloxanes: *ab initio* molecular orbital calculations", *Surface and Interface Analysis*, 2002, 34, pp. 601-605.

* cited by examiner

*Primary Examiner*—Trung Dang
(74) *Attorney, Agent, or Firm*—Kobovcik & Kubovcik

(57) ABSTRACT

Method for forming a low dielectric constant structure on a semiconductor substrate by CVD processing. The method comprises using a precursor containing chemical compound having the formula of (R1-R2)n-Si—(X1)4-n, wherein X1 is hydrogen, halogen, acyloxy, alkoxy or OH group, R2 is an optional group and comprises an aromatic group having 6 carbon atoms and R1 is a substituent at position 4 of R2 selected from an alkyl group having from 1 to 4 carbon atoms, an alkenyl group having from 2 to 5 carbon atoms, an alkynyl group having from 2 to 5 carbon atoms, Cl or F; n is an integer 1-3. The present precursors allow for a lowering of the electronic dielectric constant compared to conventional dielectric materials, such as silicon dioxide or phenyl modified organo-containing silicon dioxide.

5 Claims, 3 Drawing Sheets

LOW-K DIELECTRIC MATERIAL

This application is a 371 of international application PCT/FI2004/000440, which claims priority based on U.S. provisional patent application Nos. 60/485,114 and 60/531,672 filed Jul. 8 and Dec. 23, 2003, respectively, which are incorporated herein by reference.

BACKGROUND OF THE INVENTION

1. Field of the Invention

The present invention relates to thin films suitable as dielectrics in IC's and for other similar applications. In particular, the invention concerns thin films comprising compositions obtainable by hydrolysis and/or condensing of one or more silicon compounds, which yield an at least partially cross-linked siloxane structure via chemical vapor deposition (CVD) methods. The invention also concerns a method for producing such films by preparing siloxane compositions by CVD deposition of suitable reactants, by applying the hydrolyzed compositions on a substrate in the form of a thin layer and by optional curing the layer to form a film.

2. Description of Related Art

Built on a semiconducting substrate, integrated circuits comprise of millions of transistors and other devices, which communicate electrically with one another and outside packaging material through multiple levels of vertical and horizontal wiring embedded in a dielectric material. Within the multilayer metallization structure, "vias" comprise the vertical wiring, whereas "interconnects" comprise the horizontal wiring. Fabricating the metallization can involve the successive depositing and patterning of multiple layers of dielectric and metal to achieve electrical connection among transistors and to outside packaging material. The patterning for a given layer is often performed by a multi-step process consisting of layer deposition, photoresist spin, photoresist exposure, photoresist develop, layer etch, and photoresist removal on a substrate. Alternatively, the metal may sometimes be patterned by first etching patterns into a dielectric, filling the pattern with metal, then subsequently chemical mechanical polishing the metal so that the metal remains embedded only in the openings of the dielectric. As an interconnect material, aluminum has been utilized for many years due to its high conductivity (and low cost). Aluminum alloys have also been developed over the years to improve the melting point, diffusion, electromigration and other qualities as compared to pure aluminum. Spanning successive layers of aluminum, tungsten has traditionally served as the conductive via material. Silicon dioxide (dielectric constant of around 4.0) has been the dielectric of choice, used in conjunction with aluminum-based and tungsten-based interconnects and via for many years.

The drive to faster microprocessors and more powerful electronic devices in recent years has resulted in very high circuit densities and faster operating speeds, which in turn have required higher conductivity metals and lower-k dielectrics (preferably below 3.0, more preferably below 2.5 dielectric constant). In the past few years, VLSI (and ULSI) processes have been moving to copper damascene processes where copper (or copper alloys) is used for the higher conductance in the conductor lines and spin-on or CVD low-k dielectrics are used for the insulating material surrounding the conductor lines. To circumvent problems with etching, copper along with a barrier metal is blanket deposited over recessed dielectric structures consisting of interconnect and via openings and subsequently polished in a processing method known as "dual damascene." The bottom of the via opening is usually the top of an interconnect from the previous metal layer or in some instances, the contacting layer to the substrate.

In addition to the dielectric IC material being photopatternable, it is also desirable that the material be easy to deposit or form, preferably at a high deposition rate and at a relatively low temperature. Once deposited or formed, it is desirable that the material be easily patterned, and preferably patterned with small feature sizes if needed. Once patterned, the material should preferably have low surface and/or sidewall roughness. It might also desirable that such materials be hydrophobic to limit uptake of moisture (or other fluids), and be stable with a relatively high glass transition temperature (not degrade or otherwise physically and/or chemically change upon further processing or when in use).

Summarizing: aside from possessing a low dielectric constant, the ideal dielectric should afford the following properties:

1) A high modulus and hardness in order to bind the maze of metal interconnects and vias together as well as abet chemical mechanical polishing processing steps.
2) Low thermal expansion, typically less than or equal to that of Al interconnects.
3) Excellent thermal stability, generally in excess of 400° C.
4) No cracking, excellent fill properties.
5) Excellent adhesion to dielectric, semiconductor, and metal materials.
6) Sufficient thermal conductivity to dissipate joule heating from interconnects and vias.
7) Material density that precludes absorption of solvents, moisture, or reactive gasses.
8) Allows well-defined vertical etch profiles at very small dimensions.
9) Low current leakage, high breakdown voltages, and low loss-tangents.
10) Stable interfaces between the dielectric and contacting materials.

By necessity, low-k materials are usually engineered on the basis of compromises. Silicate-based low-k materials can demonstrate exceptional thermal stability and usable modulus but can be plagued by brittleness and cracking. In contrast, organic materials often show improved material toughness, but at the expense of increased softness, lower thermal stability, and higher thermal expansion coefficients. Porous materials sacrifice mechanical properties and possess a strong propensity for absorbing chemicals used in semiconductor fabrication leading to reliability failures. Fluorinated materials can induce corrosion of metal interconnects, rendering a chip inoperative. Universally, low-k materials sacrifice mechanical robustness and thermal conductivity with respect to their pure silicon dioxide analogues, making integration into the fabrication flow very challenging.

Further, known materials comprising exclusively inorganic bonds making up the siloxane matrix are brittle and have poor elasticity at high temperatures.

In the published International Patent Application No. WO03/015129, organosilicone low-k dielectric precursors are described useful for producing porous, low-k dielectric, SiOC thin films, wherein the organosilicon precursor comprises at least one cleavable, organic functional group that upon activation rearranges, decomposes and/or cleaves as a highly volatile liquid and/or gaseous by-product. Other organosilicone precursors comprising Si—O—C-in-ring cyclic siloxane compounds for use as precursors for forming insulator films by CVD are described in U.S. Pat. No. 6,440,876. When these siloxane precursors are applied to the surface of a semiconductor or integrated circuit, they will react on the wafer surface forming a dielectric film. The ring opening polymerization of these cyclic compounds forms a dielectric film or layer that will have a k value between 2.0 and 2.5.

U.S. Pat. No. 6,242,339 discloses an interconnection structure, in which a phenyl group, bonded to a silicon atom, is introduced into silicon dioxide-in the organic-containing silicon dioxide as a material for the interlevel insulating film. Such a film can be processed as well as a conventional CVD oxide film, has a relative dielectric constant as low as that of an HSQ film, and can adhere strongly to organic film, oxide film or metal film. According to the patent, the number of devices that can be integrated within a single semiconductor integrated circuit can be increased without modifying the conventional semiconductor device manufacturing process to provide a high-performance semiconductor integrated circuit, operative at a high speed and with lower power dissipation.

However, in spite of advantages achieved by using the known precursors, there are still disadvantages of the known methods of their manufacture. First, the manufacture of these precursors is inefficient because the chemical reactions have low yields, and the process is expensive and produces toxic byproducts. Further, it is difficult to eliminate redimerization of the reactive intermediates. When deposited along with polymers, these dimers decrease the thermal stability and mechanical strength of the film. Moreover, materials currently reaching dielectric constant less than 2.5 are typically highly porous, which makes the integration of such materials very difficult.

Thus, the prior art contains no examples of dielectric material precursors for semiconductor manufacture, which have desired properties of low dielectric constant with low porosity, high thermal stability, and low cost.

SUMMARY OF THE INVENTION

It is an object of the present invention to eliminate the problems of the known technical solutions and to provide novel low dielectric constant thin films, which have excellent mechanical and thermal properties.

It is a second object of the invention to provide methods of producing poly(organo siloxane) compositions, which are suitable for the preparation of thin films having low dielectric constant. Materials providing dielectric constant values of <2.7, <2.5 and <2.3 are also claimed.

It is a third object of the invention to provide a method of patterning dielectric films in semiconductor devices.

It is a fourth object of the invention to have precursor monomers, which allow the control electronic, ionic and orientational polarizations of the material and furthermore tunability of dielectric constant of the thin film.

It is still a fifth object of the invention to provide a method to meet all previous objectives through novel molecules for forming of low dielectric constant material formed by a CVD (Chemical Vapor Deposition) method.

These and other objects, together with the advantages thereof over the known dielectric thin films and methods for the preparation thereof, which shall become apparent from specification which follows, are accomplished by the invention as hereinafter described and claimed.

The present invention is based on the concept of providing a poly(organo siloxane) material, which exhibits both inorganic and organic bonds, for use in a CVD process for producing low-k dielectric materials, which comprise, optionally cured and at least partially cross-linked, siloxane composition to give a product which has excellent strength properties and good heat-resistance. The inorganic cross-links are based on the conventional silicon-to-oxygen bonds of a siloxane material. However, in addition to these basically inorganic and partially inflexible bonds, the novel materials may also have organic inter- and intra-chain links formed by the carbon-to-carbon bonds. These bonds are derived from the reactions of unsaturated groups, such as alkenyl or alkynyl groups, with other unsaturated groups.

The key differentiation of the current material compared to others is that low dielectric constant can be achieved without pore generation into the material. Instead, the material is designed based on the materials with electronic, ionic and orientational polarizations are sufficient to achieve low dielectric constant thin film materials, while simultaneously maintaining the all mechanical and thermal requirements set by integrated circuits manufacturing processes and in general related industry.

The design of the precursor molecules was based on the screening made molecular modeling methods. For example, this invention talks about the use of 6-, 8-, or 10-membered aromatic and non-aromatic ring structures to obtain the desired properties. Use of mono- and polycyclic (inclusive of bridged structures) ring structures are also disclosed. Saturated and unsaturated molecules are also covered.

The invention is based on the finding that it is possible to incorporate by chemical vapour deposition a bulky organic moiety into a dielectric material to reduce density and to introduce inherent microporosity using certain precursors, which comprise a hydrocarbyl radical bonded to the silicon atom of silane compounds, said hydrocarbyl radical being bonded to the silicon atom by means of a bond which is not cleaved at the conditions during the CVD processing or during any other processing step necessary for producing a layered structure. Such processing steps include heat and chemical processing.

In one aspect of the invention, a method for forming a low dielectric constant structure on a semiconductor substrate by CVD processing is provided, comprising the steps of:

introducing a material gas into a reaction chamber for CVD processing wherein a semiconductor substrate is placed, said material gas comprising a silicon-containing chemical compound having the formula of $(R^1\text{—}R^2)n\text{-Si—}(X^1)_{4-n}$, wherein $X^1$ is a hydrogen, halogen, acyloxy, alkoxy or OH group, $R^2$, which is optionally present in the compound, is an aromatic group having 5 to 7 carbon atoms, and $R^1$ is a substituent at position 4 of $R^2$, or a group directly linked to Si, selected from an alkyl group having from 1 to 4 carbon atoms, an alkenyl group having from 2 to 5 carbon atoms, an alkynyl group having from 2 to 5 carbon atoms, Cl or F, n is an integer 1 to 3; and forming a silicone polymer film on the semiconductor substrate by activating a polymerization reaction in the reaction chamber where the material gas is present until the relative dielectric constant of the silicone polymer film is lower than a predetermined value.

Thus, $R^2$ is an optional spacing unit, which separates and connects the $R^1$ residue with the silicon atom.

Another aspect of the invention, comprise the steps of:

introducing a material gas into a reaction chamber for CVD processing wherein a semiconductor substrate is placed, said material gas comprising a silicon-containing chemical compound having the formula of $(R^1\text{—}R^2)_n\text{—Si—}(X^1)_{4-n}$, wherein
each $X_1$ is independently selected from hydrogen and inorganic leaving groups,
$R_2$ is an optional group and comprises alkylene having 1 to 6 carbon atoms or arylene,
$R_2$ is a polycycloalkyl group and
n is an integer 1 to 3; and
forming a silicone polymer film on the semiconductor substrate by activating a polymerization reaction in the reaction chamber where the material gas is present until the relative dielectric constant of the silicone polymer film is lower than a predetermined value.

The materials presented in this invention provide several advantages over the known art for producing, by CVD methods, low-dielectric constant applications. The precursors have excellent thermal properties and withstand the conditions of CVD process. The mechanical properties of films prepared by CVD processing of the present precursors are excellent and, in particular, they allow for an adjustment of the electronic dielectric constant of the film structure. Furthermore, the effect of ionic and orientational dielectric constants can be minimized.

DETAILED DESCRIPTION OF THE INVENTION

Next, the invention will be examined more closely by means of the following detailed description and with reference to a number of working examples.

Figure 1:
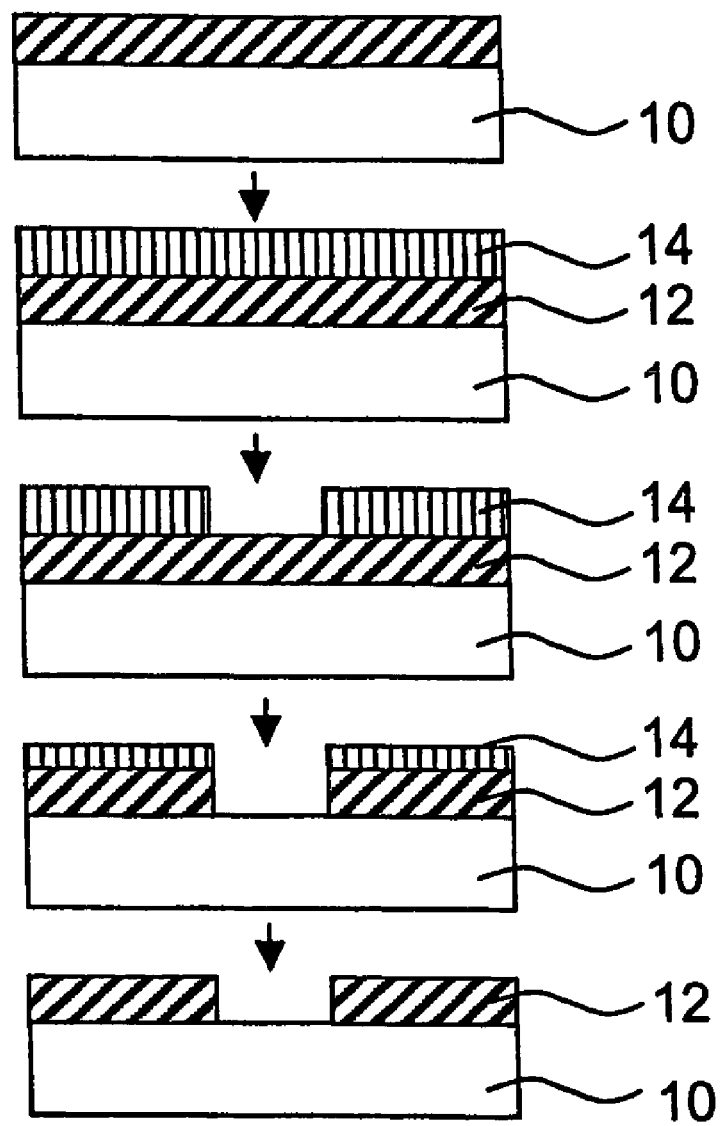
FIG. 1 shows in a schematic fashion the various steps of a process for patterning a dielectric film.

The present invention provides for the use of a novel type of precursors for the production by the CVD process for making polymers with low dielectric constants and high thermal stability. Thus, basically, the present invention is directed to the formation of a low-k dielectric thin film by a process, which comprises chemical vapor depositing on a substrate, a low-k dielectric thin film from an organosilicon composition containing at least one cleavable organic functional group that upon activation rearranges and cleaves as a highly volatile liquid and/or gaseous species, to produce a thin film having a dielectric constant of less than 3.0.

The polymers can be used for making integrated circuits. Additionally, the invention includes methods for making polymers for integrated circuit manufacture using novel fluorinated siloxanes, fluorinated siloxanes, or fluorocarbons, each containing a fluorinated aromatic moiety. Furthermore, the invention includes integrated circuits comprising low dielectric constant polymers made using fluorinated siloxanes, fluorinated siloxanes, or fluorocarbons, each containing a fluorinated aromatic moiety.

Basically, according to one embodiment, the invention comprises using in CVD processing of semiconductor substrates a chemical compound having the formula of

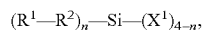

wherein $X^1$ is hydrogen, halogen, acyloxy, alkoxy or OH group, $R^2$, which is a spacer group which optionally is present in the compound, stands for an aromatic group having typically 5 to 7 carbon atoms, typically 6 carbon atoms, and $R^1$ is a substituent at position 4 of $R^2$, or a group directly linked to Si, selected from an alkyl group having from 1 to 4 carbon atoms, an alkenyl group having from 2 to 5 carbon atoms, an alkynyl group having from 2 to 5 carbon atoms, Cl or F, n being an integer 1 to 3. Preferably n is 1.

Some suitable compounds of the above kind are indicated in the below examples.

However, more generally speaking, the present compounds of the above formula comprise an $R^1$ residue which is a carbon group having from 1 to 30 carbons, in particular 1 to 15 carbons. The carbon chain of $R^1$ can be fluorinated or perfluorinated. $R^1$ can be branched carbon chain. It is, in particular, selected from $CF_3$, $CF_2CF_3$, $CF_2CF_2CF_3$, $CF_2OH$, $CF_2CF_2OH$; from carbon chains having a carbon-carbon double bond and from 2 to 5 carbons; from vinyl groups, acrylic group, alkenyl groups having from 1 to 4 carbons; from aromatic groups having from 5 to 7 carbon atoms, typically 5 or 6 carbon atoms.

The polycycloalkyl siloxane precursors used according to the invention have the general formula I

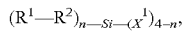    I wherein
each $X^1$ is independently selected from hydrogen and inorganic leaving groups,
$R^2$ is an optional group and comprises alkylene having 1 to 6 carbon atoms or arylene,
$R^1$ is a polycycloalkyl group and n is an integer 1 to 3
In the group having the formula

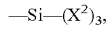

$X_2$ is a halogen,

According to another preferred embodiment, $R^1$ is selected from $CH_2$, $CH_2CH_3$, $(CH_2)_2CH_3$, $(CH_2)CF_3$, $CH_2CH_2OH$ or $CH_2CF_2OH$.

In the above formulas, $X^1$ and $X^2$ are, for example, independently selected from chlorine. They can also independently be selected from the group consisting of hydrogen, alkoxy groups, acyloxy groups, OH groups. In particularly, $X^1$ is an ethoxy group.

$R^2$ is an optional spacer group. It is present in cases where $R^1$ is capable of withdrawing electrons from the C—Si bond so as to weaken it. Typically, $R^1$ and $R^2$ are together bulkier than a phenyl group. $R^2$ is generally selected from aromatic groups having from 5 to 7 carbon atoms, in particular 5 or 6 carbon atoms, and non-aromatic ring structures having from 5 to 10 carbons. Thus, to give an example, $R^2$ can be an optionally substituted phenyl group. $R^2$ is, according to an embodiment, further substituted at positions 3 and 5. The substituent at these positions can be $CF_3$.

The polycyclic alkyl group has from 9 to 16 carbon atoms, and it comprises preferably a cage compound (as defined above). The ring structure can be substituted with 1 to 3 alkyl substitutents, which optionally carry 1 to 6 halogen substitutents, e.g. chloro, fluoro or bromo. In the case of $R^1$ standing for a polycyclic alkyl group, $R^2$ is an optional group and comprises alkylene having 1 to 6 carbon atoms or arylene, and each $X^1$ is independently selected from hydrogen and inorganic leaving groups. $R^1$ is bonded to the silicon atom via an alkylene chain, in particular an alkylene chain selected from methylene, ethylene and propylene, or an arylene group, in particular phenylene. The inorganic leaving group is preferably selected from halogens, such as chlorine, bromine or fluorine.

The compounds are used in conventional CVD processing. Thus, the precursors are evaporated (if they normally—at normal temperature and pressure—are present as liquids or solids) or employed as gases. The CVD processing comprises the steps of introducing the material gas into a reaction chamber for CVD processing, wherein a semiconductor substrate is placed, and forming a silicone polymer film on the semiconductor substrate by activating a polymerization reaction in the reaction chamber where the material gas is present until the relative dielectric constant of the silicone polymer film is lower than a predetermined value of 3.0, preferably less than 2.5.

Conventionally, the temperature of the CVD process is about 20 to 500 deg C., preferably about 50 to 450 deg C. The pressure can be atmospheric, although it is preferred to operate the process at reduced pressure, generally at an absolute pressure of 0.01 to 100 mbar, in particular 0.1 to 10 mbar. The use of an inactive or inactive gas as a protecting and purging gas is also preferred.

It is required that the compounds and precursors are stable at the CVD processing conditions, which means that they should be capable of vaporization and reaction at temperatures up to 400 or more deg C. (below 500 deg C.), at which temperatures, the C—Si bond linking the $R^1$—$R^2$ moiety (or $R^1$ moiety, in cases where there is no spacing group) to the silicon atom is uncleaved.

During the CVD processing and/or during any following processing step, in addition to the precursors, other components can be employed. Thus, e.g., additional reactive compounds can be applied. Such compounds are exemplified by hydrogen peroxide, hydrogen, carbon monoxide, and carbon dioxide, which can be used in the form of gases. Other gases that can be employed as auxiliary components include argon, nitrogen and foaming gases.

The invention comprises a number of preferred embodiments. These include the following (the percentages refer to atom-%):

A poly(organo siloxane) compound formed via CVD process comprising a repeating Si—O backbone, carbon chain crosslinking groups and —$R^1$—$R^2$ bound to from 5% to 60% of the silicon atoms in the Si—O backbone, wherein $R^2$ is an optionally present spacer group, e.g. an aromatic group having 6 carbon atoms, and $R^1$ is a hydrocarbyl radical, as defined above, for instance constituting a substituent at position 4 of $R^2$ or directly linked to the silicon atom.

According to a particular embodiment of this alternative, the Si—O backbone further comprises $R^3$ groups bound to from 5% to 25% of the silicon atoms in the Si—O backbone, wherein $R^3$ is an alkyl group having from 1 to 10 carbon atoms, an alkenyl chain or aryl group. These $R^3$ groups can be introduced by employing precursors of the kind disclosed in PCT/FI03/00036, the disclosure of which is herewith incorporated by reference. Thus, at least two different kinds of additional silane reactants can be used according. The first group of silane reactants comprises compounds containing an unsaturated hydrocarbon residue, which will provide for organic cross-linking. The second group of silane reactants comprises compounds containing at least one aryl group. These hydrocarbyl radicals are bonded to the silicon atom of the silane compound (also called a monomeric silicon compound in the following). The reactants are hydrolysed to form an organosiloxane polymer. Therefore, they contain, in addition to the hydrocarbyl radical, also a hydrolysable group bonded to the silicon atom of the silane. In addition to the above reactants, reactants of a third group of silane compounds can be used, which contain a hydrolysable group and an organic saturated group, such as an alkyl group.

Another poly(organo siloxane) compound formed according to the present invention via the CVD method comprises a repeating Si—O backbone, —$R^1$—$R^2$ bound to from 25% to 60% of the silicon atoms in the Si—O backbone, wherein $R^2$ is an optionally present spacer group, e.g. an aromatic group having 6 carbon atoms, and $R^1$ is a hydrocarbyl radical, as defined above, for instance constituting a substituent at position 4 of $R^2$, and $R^3$ bound to from 5% to 60% of the silicon atoms, wherein $R^3$ is an alkenyl group having from 2 to 5 carbon atoms, acrylic group or epoxy group.

This compound can further comprise $R^4$ groups bound to from 5 to 60% of the silicon atoms of the Si—O backbone, wherein $R^4$ is an alkyl group having from 1 to 30 carbon atoms, in particular 1 to 15 carbon atoms.

The invention provides, for example, an integrated circuit having a layer with areas of an electrically conductive first material and an electrically insulating second material, wherein the second material is a poly(organo siloxane) compound deposited via CVD method and comprising a repeating Si—O backbone, carbon chain crosslinking groups and —$R^1$—$R^2$ bound to from 5% to 60% of the silicon atoms in the Si—O backbone, wherein $R^2$ is an optionally present spacer group, e.g. an aromatic group having 6 carbon atoms, and $R^1$ is a hydrocarbyl radical, as defined above, for instance constituting a substituent at position 4 of $R^2$ or directly linked to the silicon atom.

The integrated circuits can be used in computers.

The poly(organosiloxane) materials prepared by CVD from the above-described compounds optionally hydrolyzed and condensed (alone with one or more other compounds) into a hybrid material having a (weight average) molecular weight of from 500 to 100,000 g/mol. The molecular weight can be in the lower end of this range (e.g., from 500 to 5,000, or more preferably 500 to 3,000) or the hybrid material can have a molecular weight in the upper end of this range (such as from 5,000 to 100,000 or from 10,000 to 50,000). In addition, it may be desirable to mix a hybrid material having a lower molecular weight with a hybrid material having a higher molecular weight.

The materials and precursors presented in this invention provide several advantages over materials and precursors applied in CVD methods for low- dielectric constant applications known from the prior-art, as will appear from the following list:

1) The organic functionalities of the precursors are stable and the moieties and the Si—C bond linking them to the silane residue will withstand the conditions of the CVD processes. Furthermore, the compounds will be stable at the further processing steps of the materials, such as high temperature curing steps, additional high temperature or otherwise challenging such wet chemical post-processing steps. During none of the above processing steps will the precursors undergo unwanted chemical reactions. The organic functional group is strongly bonded to the silicon from its alpha carbon as well as potentially from the organo functional group through, for example, organic cross-linking.

2) Since organic functionalities are bonded to silicon dioxide matrix the final material results in better mechanical properties than purely organic films made through CVD processes.

3) The precursors allow an adjustment of electronic dielectric constant of the formed dielectric film structure. Especially, they allow to lower the electronic dielectric constant compared to conventional dielectric materials such as silicon dioxide or phenyl modified organo-containing silicon dioxide as described by Aoi et al. (U.S.

Pat. No. 6,242,339). The ability for the adjustment comes, for example, from the capability to attach fluorine or fluorine containing moieties to organic functional group such as to phenyl group. The precursors also generate so called micro porosity or more specifically intramolecular porosity into the silicon dioxide in which the pore size radius is approximately 1 nm or smaller. The pore volume in the material is less than 15 volume-%. Therefore, the materials described by the invention are not porous as are other low-k hybrid organo-silicon materials also known as organo-silicate-glasses or OSG, which pore size radius is typically from few nm to up to tens of nanometers and pore volume is higher than 20% or more typically higher than 35%.

4) CVD processing through the precursors described in the invention high organics concentration is achievable without scarifying thermal and mechanical properties of the formed dielectric film structure so that the effect of ionic and orientational dielectric constants are minimized which are mainly dominated by silicon oxide matrix.

5) CVD precursors based on the invention provide high contact angle against water or aqueous solutions and contact angle higher than 90 degrees or more specifically higher than 100 degrees whereas with conventional CVD silicon dioxide materials contact angle with water is typically less than 50 degrees.

The above materials are employed, e.g., in methods for making an integrated circuit, comprising providing alternating areas of electrically insulating and electrically conducting materials within a layer on a semiconductor substrate. The electrically insulating material comprises a poly(organo siloxane) compound deposited via CVD method comprising a repeating Si—O backbone, carbon chain crosslinking groups and —$R^1$—$R^2$ bound to from 5% to 60% of the silicon atoms in the Si—O backbone, wherein $R^2$ is—optionally, as explained above—an aromatic group having 6 carbon atoms and $R^1$ is a substituent at position 4 of $R^2$ selected from an alkyl chain having from 1 to 4 carbons, an alkenyl group having from 2 to 6 carbons or OH.

Generally, the electrically insulating material is deposited via CVD method, baked and patterned, with the electrically conductive material being deposited in removed areas of the patterned dielectric. The electrically conductive material comprises for example copper.

The above method is, e.g., a dual damascene process.

The deposition and patterning processes are described in the following:

FIG. 1 gives an example of a typical process, which can be used for patterning a dielectric film provided by the present invention. First, a dielectric layer film 12 is deposited on a wafer substrate 10 by chemical vapor deposition. Next, a removable, photosensitive "photoresist" film 14 is spun onto the wafer substrate 10. Afterward, the photoresist 14 is selectively exposed through a mask, which serves as a template for the layer's circuit pattern and is subsequently developed (developer applied to remove either exposed or unexposed areas depending upon the type of resist). The photoresist is typically baked after spin, exposure, and develop. Next, the layer film is etched in a reactive plasma, wet bath, or vapor ambient in regions not covered by the photoresist to define the circuit pattern. Lastly, the photoresist 14 is stripped. The process of layer deposition, photoresist delineation, etching, and stripping is repeated many times during the fabrication process.

Figure 2:
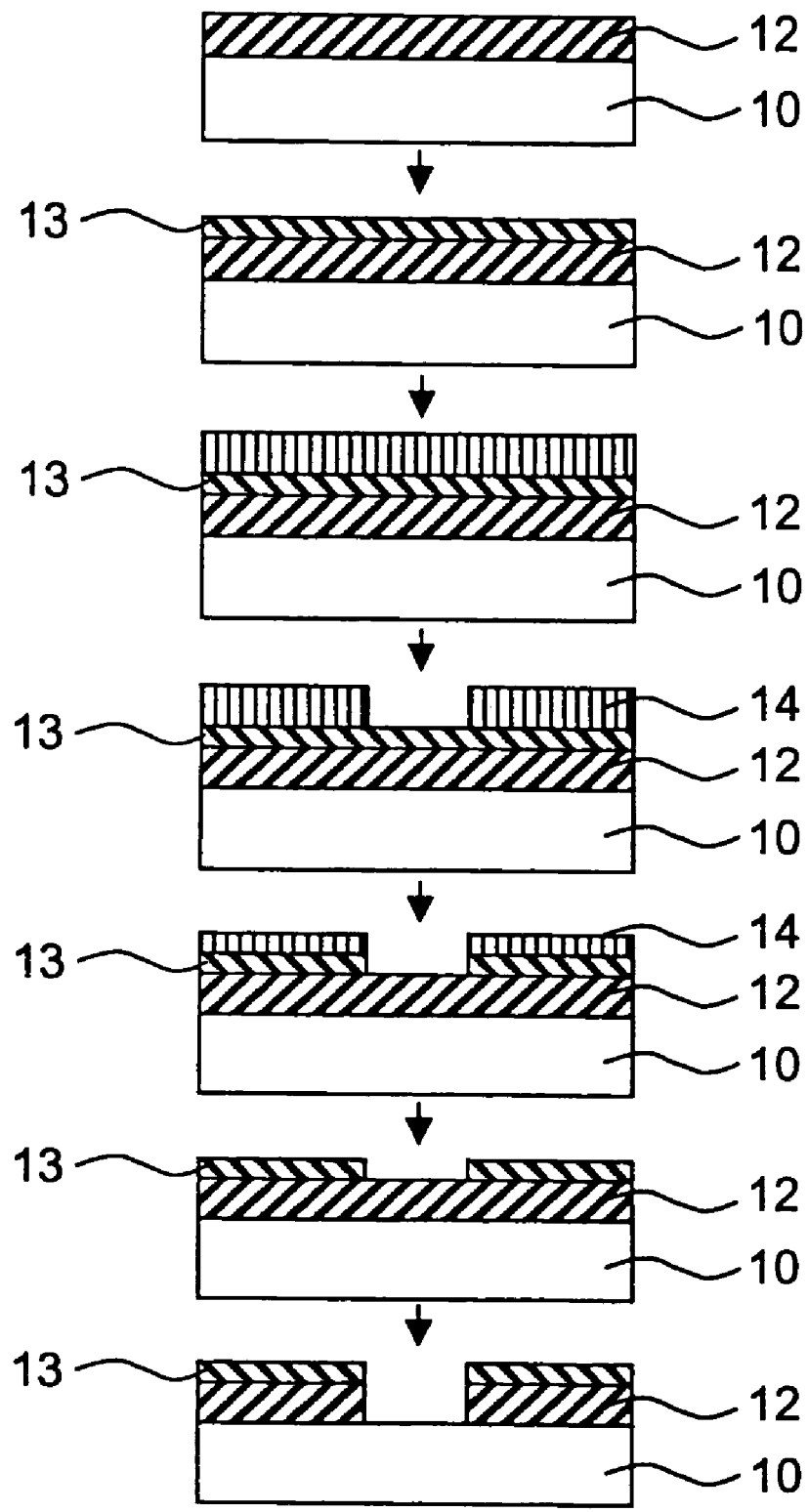
FIG. 2 gives a similar depiction of an alternative process in which a hard mask is inserted between the layered film and the photoresist.

Because photoresist can unacceptably erode during the etch process or may not be able to be adequately delineated within device specifications, a hard mask is sometimes inserted between the layer film and the photoresist (the materials of the invention could also be used for making such a hard mask). FIG. 2 illustrates this typical method, which is similar to the dielectric patterning process described previously in relation to FIG. 1. The layer film could be metal, semiconductor, or dielectric material depending on the application. As can be seen in FIG. 2, a substrate 10 is provided on which is deposited by CVD a layer film 12. On film 12 is deposited a hard mask 13. On the hard mask 13 there is deposited a photoresist material 14. The photoreist is exposed and developed so as to selectively expose the underlying hard mask 13. Then, as can be further seen in FIG. 2, the hard mask 13 is etched via the exposed areas in photoresist 14. Thereafter, the photoresist is removed and the dielectric film 12 is etched by using the hard mask 13 as the pattern mask.

Figure 3A:
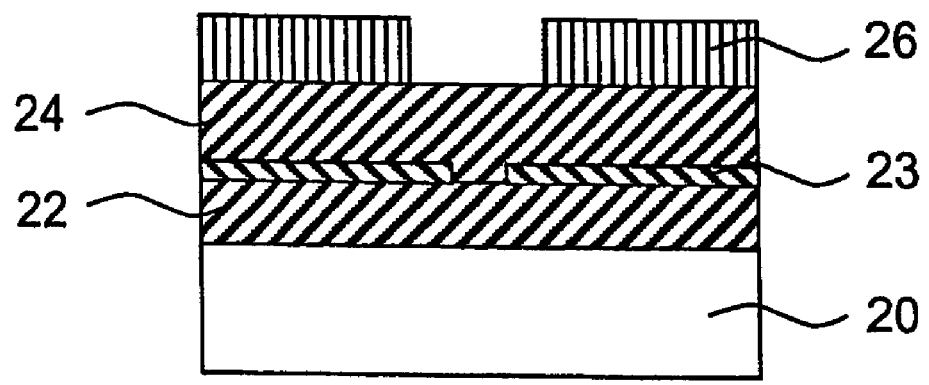
FIG. 3 shows an embodiment of the "dual damascene" process combining dielectric etches and hard masks to form trenches and vias to contain metal interconnects.
Figure 3B:
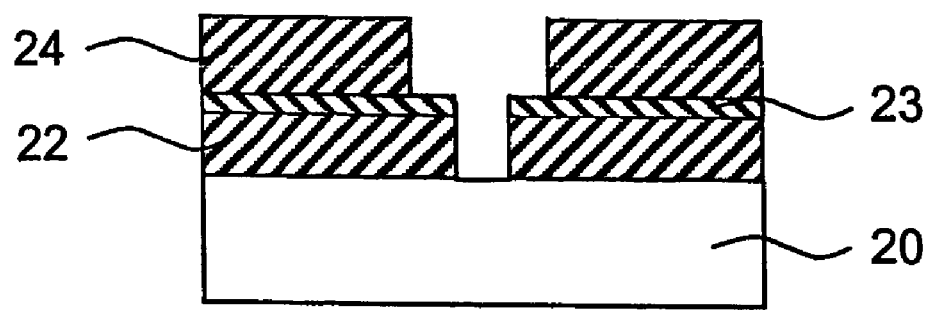

The "dual damascene" process used in integrated circuit application combines dielectric etches and sometimes hard masks to form trenches and vias to contain metal interconnects. FIG. 3 demonstrates one implementation of the technique. From the bottom up in FIG. 3$a$, the stack is made up of a substrate 20, a dielectric film 22, a hard mask 23, a second dielectric film 24, and a patterned photoresist layer 26. After etching and photoresist strip, a dual-width trench feature is formed as shown in FIG. 3$b$. The openings are then filled with metal and subsequently polished, leaving metal only within the openings.

The procedures shown in FIGS. 1-3 are often repeated many times during integrated circuit application, which adds to the cost of the circuit and degrades yield. Reducing the number of steps, such as implementing a photopatternable dielectric material of the present new kind, which obviates the need for photoresist and etching steps, has huge benefits to the circuit manufacturer.

In the following, the synthesis of some suitable compounds is disclosed in more detail:

Synthesis of Molecules (#1) 4-(trifluoromethyl)phenyl trichlorosilane,
4-$(F_3C)C_6H_4SiCl_3$ Preparation:

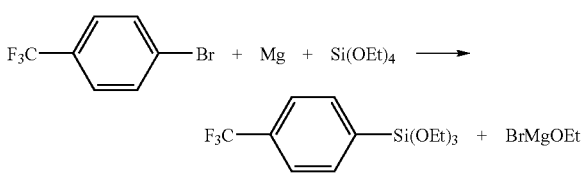

96.24 g (0.427 mol) 4-(trifluoromethyl)phenyl bromide, 10.38 g (0.427 mol) magnesium, and a small amount of iodine are stirred for half an hour. 356.78 g (382 ml, 1.708 mol) $Si(OEt)_4$ is added to solution. $Et_2O$ is added until exothermic reaction occurs (~200 ml) and the solution is refluxed for over night. $Et_2O$ is evaporated off and 250 ml n-heptane is added. Mg-salts are filtered off. n-heptane is evaporated and remaining 4-$(F_3C)C_6H_4Si(OEt)_3$ is purified by distillation. B.p. 68° C./1 mbar. Yield 50.22 g (38%).

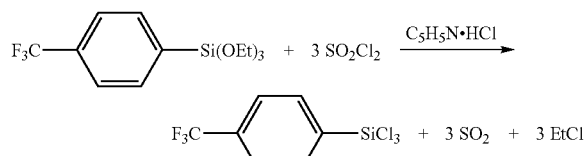

50.22 g (0.163 mol) 4-(trifluoromethyl)phenyl triethoxysilane, 83 mL (1.140 mol, 135.62 g) thionylchloride and 2.45 g (0.021 mol) pyridinium hydrochloride were refluxed and stirred for 16 h. Excess of SOCl$_2$ was evaporated and residue was fractionally distilled to obtain 37 g (81%) 4-(trifluoromethyl)phenyl trichlorosilane. B.p. 44° C./4.0 mbar.

Characterization:

4-(trifluoromethyl)phenyl triethoxysilane, 4-(CF$_3$)C$_6$H4Si(OEt)$_3$

NMR (Et$_2$O):
$^{29}$Si: −63.0 ppm
$^{13}$C: 139.3 ppm (C$_1$) 137.4 ppm (C$_{2,6}$) 126.4 ppm (C$_{3,5}$) 134.4 ppm (qu, C$_4$), $^2J_{C4-F}$ 31.7 Hz 126.6 ppm (qu, C$_7$), $^1J_{C7-F}$ 271.4 Hz 60.8 ppm (C$_8$) 20.0 ppm (C$_9$)

4-(trifluoromethyl)phenyl trichlorosilane, 4-(CF$_3$)C$_6$H4SiCl$_3$

NMR (Et$_2$O):
$^{29}$Si: −1.5 ppm
$^{13}$C: 138.1 ppm (C$_1$) 136.0 ppm (C$_{2,6}$) 127.7 ppm (C$_{3,5}$) 137.0 ppm (qu, C$_4$), $^2J_{C4}$-F 33.3 Hz 125.9 ppm (qu, C$_7$), $^1J_{C7-F}$ 272.2 Hz
$^{19}$F: −65.3 ppm (#2) 3,5-Bis(trifluoromethyl)phenyl trichlorosilane, 3,5-(F$_3$C)$_2$C$_6$H$_3$SiCl$_3$ Preparation:

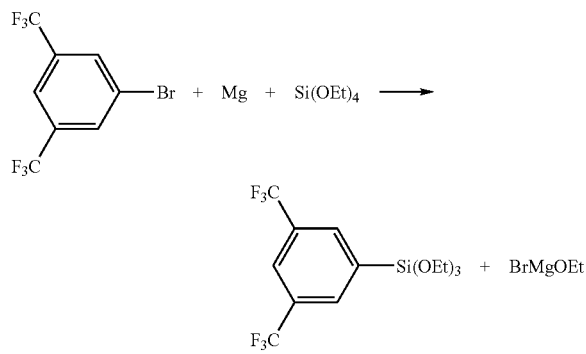

125.11 g (0.427 mol) 3,5-bis(trifluoromethyl)phenyl bromide, 10.38 g (0.427 mol) magnesium, and a small amount of iodine are stirred for half an hour. 356.78 g (382 ml, 1.708 mol) Si(OEt)$_4$ is added to solution. Et$_2$O is added until exothermic reaction occurs (~200 ml) and the solution is refluxed for over night. Et$_2$O is evaporated off and 250 ml n-heptane is added. Mg-salts are filtered off. n-heptane is evaporated and remaining 3,5-(F$_3$C)$_2$C$_6$H$_3$Si(OEt)$_3$ is purified by distillation. B.p. 80° C./0.8 mbar. Yield 78.72 g (52%).

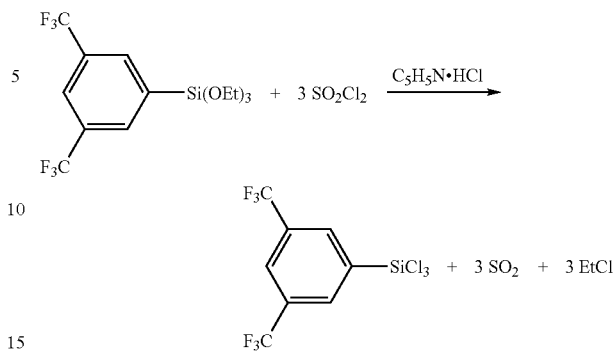

61.35 g (0.163 mol) 3,5-bis(trifluoromethyl)phenyl triethoxysilane, 83 mL (1.140 mol, 135.62 g) thionylchloride and 2.45 g (0.021 mol) pyridinium hydrochloride were refluxed and stirred for 16 h. Excess of SOCl$_2$ was evaporated and residue was fractionally distilled to obtain 44.2 g (78%) 3,5-bis(trifluoromethyl)phenyl trichlorosilane. B.p. 41° C./3.1 mbar.

(#3) Pentafluorophenyl methyl trichlorosilane, C$_6$F$_5$CH$_2$SiCl$_3$

Preparation:

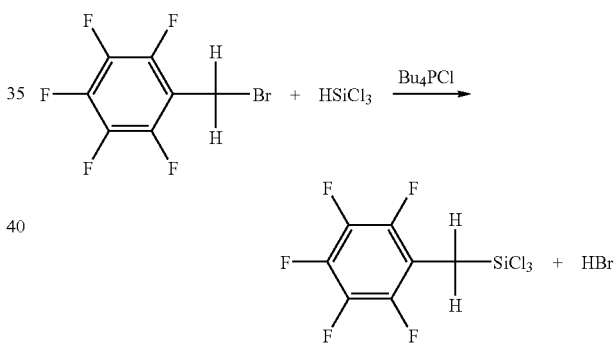

106.29 g (0.407 mol) pentafluorophenylmethyl bromide, 1.20 g (0.004 mol) Bu$_4$PCl, and 187.55 g (140 ml, 1.385 mol) HSiCl$_3$ were added to high pressure vessel. Solution was heated to 150° C. for four hours. Excess HSiCl$_3$ was evaporated and C$_6$F$_5$CH$_2$SiCl$_3$ was purified by distillation. B.p. 56° C./2.4 mbar. Yield 91.18 g (71%).

Other applicable precursors based on molecular modeling are but not limited to:

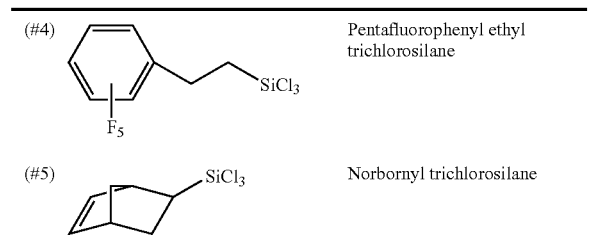

-continued

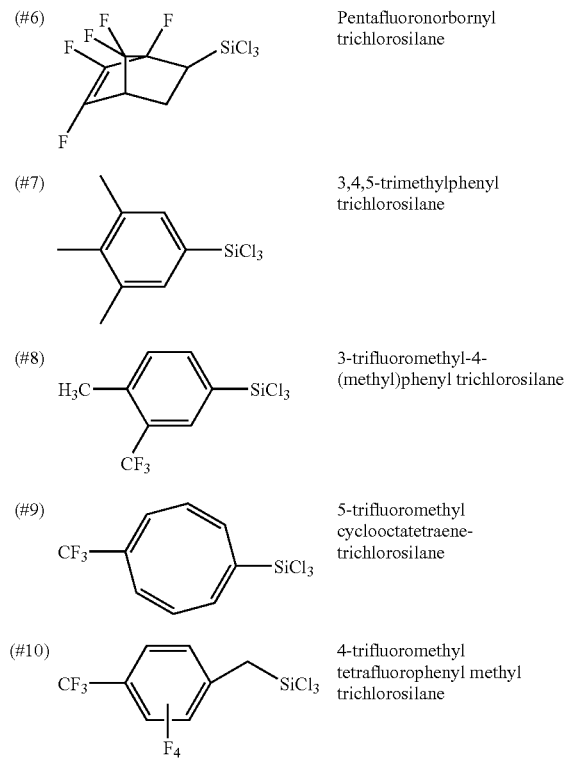

| | | |
|---|---|---|
| (#6) | | Pentafluoronorbornyl trichlorosilane |
| (#7) | | 3,4,5-trimethylphenyl trichlorosilane |
| (#8) | | 3-trifluoromethyl-4-(methyl)phenyl trichlorosilane |
| (#9) | | 5-trifluoromethyl cyclooctatetraene-trichlorosilane |
| (#10) | | 4-trifluoromethyl tetrafluorophenyl methyl trichlorosilane |

All above-mentioned monomers can be applied in organosilanol, organoalkoxysilane and organochlorosilane forms or in their combinations. In addition the number of organic functionalities in the above-mentioned precursors may vary from 1-3 also in such away that the organic functionalities are different from each other.

Formation of Dielectric Film Via the CVD Process

EXAMPLE A

In one embodiment, the present invention relates to a chemical vapor deposition (CVD) process and more preferably a plasma enhanced chemical vapor deposition (PECVD) process for forming a low-k dielectric thin film on a substrate, including the steps of: placing the substrate in a chemical vapor deposition apparatus, introducing at least one vaporized organosilicon precursor comprising at least one cleavable organic functional group into-the apparatus; transporting the organosilicon- vapor into a chemical vapor deposition zone containing a substrate, optionally using a carrier gas to effect such transport; contacting the organosilicon vapor with the substrate under chemical vapor deposition conditions to deposit a thin film comprising an organosilicon composition; and activating the organosilicon thin film to produce a low-k dielectric thin film. The activation step is carried out under conditions sufficient to effect the removal of at least a portion of the cleavable, organic functional groups, and optionally to activate at least a portion of cross-linking functional groups (if present), to produce a thin film having a dielectric constant of less than 2.7. Useful sources of activation include but are not limited to chemical generation of free radicals, plasma, pulsed plasma, chemical quenching agents, co-reactants, initiators and combinations thereof.

In method A, a low-k dielectric material structure containing organic silicon dioxide composition is formed by a CVD process using a reactive gas containing 4-(trifluoromethyl) phenyl triethoxysilane. Therefore, a functional organic silicon dioxide structure is formed in which 4-(trifluoromethyl) phenyl group is bonded to a silicon atom. Accordingly to the method a conventional CVD system can be applied so that organic content in such a film can be 40 at.-% or higher and respectively dielectric constant of the of the material structure is 2.7 or lower and more preferably less than 2.4. Alternatively, all above-mentioned precursors can be applied either alone or in combination with each other or with conventional CVD precursors such as tetraethylorthosilicate or methyl triethoxysilane. The film can adhere strongly to organic film, hybrid organic-inorganic film, metal film, high-k dielectric, barrier or liner films or other similar films. The deposited film structure also exhibits heat resistance higher than 400 deg C. and higher hydrophobicity than conventional silicon dioxide dielectric film structures.

EXAMPLE B

The materials are deposited as in example A and the formed films are further annealed at elevated temperatures in air, nitrogen, argon, forming gas or vacuum. The curing temperature is preferably higher than the deposition temperature in the deposition step described in the method A and can be as high as 600 deg C. but is not limited to that.

In this embodiment, the present invention relates to a chemical vapor deposition (CVD) process and more preferably a plasma enhanced chemical vapor deposition (PECVD) process for forming a low-k dielectric thin film on a substrate, including the steps of: placing the substrate in a chemical vapor deposition apparatus, introducing at least one vaporized organosilicon precursor comprising at least one cleavable organic functional group into the apparatus; transporting the organosilicon vapor into a chemical vapor deposition zone containing a substrate, optionally using a carrier gas to effect such transport; contacting the organosilicon vapor with the substrate under chemical vapor deposition conditions to deposit a thin film comprising an organosilicon composition; and annealing the organosilicon thin film to produce a low-k dielectric thin film.

In yet a further embodiment, the present invention relates to a CVD process and more preferably a PECVD process, for forming low-k dielectric thin films on a substrate, including the steps of: placing the substrate in a chemical vapor deposition apparatus; introducing at least one vaporized organosilicon precursor comprising at least one cleavable organic functional group and at least one alkyl group into the apparatus; transporting the organosilicon vapor into a chemical vapor deposition zone containing a substrate, optionally using a carrier gas to effect such transport; contacting the organosilicon vapor with the substrate under chemical vapor deposition conditions to deposit a thin film comprising an organosilicon composition; annealing the organosilicon thin film to produce a low-k dielectric thin film.

EXAMPLE C

The materials are deposited as in example A and the formed films are radiation exposed (UV, DUV, Extreme UV, IR or e-beam) prior to further treatments such as curing at elevated temperatures in air, nitrogen, argon, forming gas or vacuum or prior second layer deposition such as metal, barrier, liner or additional dielectric layer deposition, which can be either regular dielectric film, low-k dielectric film or high-k dielectric film. The exposed can be applied through a mask or reticle or alternatively in a flood exposure manner. The exposure step can also be followed by a development step or elevated temperature-curing step.

Thus, in addition to thermally and plasma-generated reactive intermediates, photon assisted precursor cracking is also part of this invention. Because specific chemical bonds have specific energies, and because these energies can be supplied as photons, electromagnetic radiation is a preferred method of practicing this invention.

According to an example method, precursors are stored in a precursor container and then flow through a pipe into a reactor tube for UV photolytic cracking of the precursor. For infrared (IR) cracking of the precursor, the reactor may be made of glass. For vacuum ultraviolet photolytic cracking of the precursor, the reactor can be made of MgF2, LiF, or CaF2. An ultraviolet (UV) source can be further used to photolytically dissociate the precursor. Alternatively, a vacuum ultraviolet (VUV) source can be used. An infrared (IR) source can be used, which heats the precursors to provide a combination of thermolytic and photolytic cracking. After cracking, the intermediates pass into a deposition chamber, which is heated by a resistive heater to prevent deposition of intermediates on the walls of the chamber. The flow of intermediates is adjusted using a flow adjuster. A wafer onto which the precursor is applied is maintained at low temperatures by a conventional cooling device, using liquid nitrogen, reverse Peltier effect, or any other cooling apparatus known in the art.

Using the photolytic method, the dissociation reaction can be very selective and efficient if appropriate photon sources are used. The photon sources can be provided by ultraviolet (UV) light generated by mercury vapor discharge or metal halide lamps. Exemplary sources of UV radiation for transport polymerization can include (1) a mercury lamp that provides from 50 to 220 mWatts/cm2 of UV ranging from 200 to 450 nm or (2) a metal halide lamp that provides from 40 to 160 mWatts/cm2 of UV ranging from 260 nm to 450 nm. These UV sources provide photon energies ranging from 2 to 5 eV, which are sufficient for generating many radical intermediates.

An alternative to conventional UV light is vacuum ultraviolet (VUV). Incoherent excimer radiation can provide a large number of UV and VUV wavelengths for photolytic processing of various chemicals. The preferred source is incoherent excimer radiation derived from dielectric barrier discharge. UV and VUV photons that are in the ranges of 3 to 5 eV are especially useful.

However, the energies of mercury vapor or metal halide UV radiation are too small to be useful for rapid transport polymerization. The desired residence time within the cracking chamber, which is the time available for photolysis should be in the range of a few milliseconds to several hundred milliseconds. Therefore, VUV is the most desirable form of energy for photon assisted transport polymerization. VUV or incoherent excimer UV sources can be provided by dielectric barrier or silent discharge.

When IR incoherent excimer irradiation is used, the conventional stainless steel or ceramic pipe or reactor used in the pyrolyzer will have to be replaced with a quartz tube or reactor. When using UV, a transparent tube can be made of any UV transparent material such as quartz, preferably a single quartz crystal. When using VUV, the transparent tube must be made of a material transparent to VWV wavelengths. Crystals of MgF2, LiF, or CaF2 are preferred.

I claim:

1. A poly(organo siloxane) compound formed via a CVD process and comprising a repeating Si—O backbone, carbon chain crosslinking groups and —$R^1$—$R^2$ bound to from 5% to 60% of the silicon atoms in the Si—O backbone, wherein $R^2$ is an aromatic group having 6 carbon atoms and $R^1$ is a substituent at position 4 of $R^2$.

2. A poly(organo siloxane) compound formed via a CVD method and comprising a repeating Si—O backbone, —$R^1$—$R^2$ bound to from 25% to 60% of the silicon atoms in the Si—O backbone, wherein $R^2$ is an aromatic group having 6 carbon atoms and $R^1$ is a substituent at position 4 of $R^2$ or a group directly linked to Si, and $R^3$ is bound to from 5% to 60% of the silicon atoms, wherein $R^2$ is an alkenyl group having from 2 to 5 carbon atoms, acrylic group or epoxy group.

3. An integrated circuit having a layer with areas of an electrically conductive first material and an electrically insulating second material, wherein the second material is a poly(organo siloxane) compound deposited via a CVD method and comprising a repeating Si—O backbone, carbon chain crosslinking groups and —$R^1$—$R^2$ bound to from 5% to 60% of the silicon atoms in the Si—O backbone, wherein $R^2$ is an aromatic group having 6 carbon atoms and $R^1$ is a substituent at position 4 of $R^2$.

4. A computer comprising an integrated circuit having a layer with areas of an electrically conductive first material and an electrically insulating second material, wherein the second material is a poly(organo siloxane) compound deposited via a CVD method and comprising a repeating Si—O backbone, carbon chain crosslinking groups and —R1—R2 bound to from 5% to 60% of the silicon atoms in the Si—O backbone, wherein R2 is an aromatic group having 6 carbon atoms and R1 is a substituent at position 4 of R2.

5. A method for making an integrated circuit, comprising providing alternating areas of electrically insulating and electrically conducting materials within a layer on a semiconductor substrate, wherein the electrically insulating material comprises a poly(organo siloxane) compound deposited via a CVD method and comprising a repeating Si—O backbone, carbon chain crosslinking groups and —R1—R2 bound to from 5% to 60% of the silicon atoms in the Si—O backbone, wherein R2 is an aromatic group having 6 carbon atoms and R1 is a substituent at position 4 of R2 selected from an alkyl chain having from 1 to 4 carbons, an alkenyl group having from 2 to 6 carbons or OH.

* * * * *